(12) United States Patent
Kim

(10) Patent No.: US 8,137,514 B2
(45) Date of Patent: *Mar. 20, 2012

(54) APPARATUS FOR MANUFACTURING STERILIZED WATER, AND PORTABLE APPARATUS FOR MANUFACTURING STERILIZED SALT SOLUTION

(76) Inventor: Chil-Young Kim, Gyeonggi-do (KR)

( * ) Notice: Subject to any disclaimer, the term of this patent is extended or adjusted under 35 U.S.C. 154(b) by 1005 days.

This patent is subject to a terminal disclaimer.

(21) Appl. No.: 11/919,151

(22) PCT Filed: Apr. 25, 2006

(86) PCT No.: PCT/KR2006/001560
§ 371 (c)(1),
(2), (4) Date: Oct. 24, 2007

(87) PCT Pub. No.: WO2006/115370
PCT Pub. Date: Nov. 2, 2006

(65) Prior Publication Data
US 2009/0314645 A1    Dec. 24, 2009

(30) Foreign Application Priority Data

Apr. 26, 2005 (KR) .................. 10-2005-0034697
Jun. 20, 2005 (KR) .................. 10-2005-0053185

(51) Int. Cl.
*C25B 11/02* (2006.01)
*C25B 1/24* (2006.01)
*C02F 1/461* (2006.01)
*C02F 1/467* (2006.01)

(52) U.S. Cl. .............. 204/271; 204/278.5; 204/289; 205/742

(58) Field of Classification Search .............. None
See application file for complete search history.

(56) References Cited

U.S. PATENT DOCUMENTS

| 4,014,766 A * | 3/1977 | Watanabe et al. ......... 205/746 |
| 5,556,523 A * | 9/1996 | Satoh et al. .............. 204/272 |
| 5,795,459 A | 8/1998 | Sweeney ................. 205/701 |
| 6,261,464 B1 * | 7/2001 | Herrington et al. ........ 210/758 |
| 6,736,966 B2 | 5/2004 | Herrington et al. ........ 210/192 |

FOREIGN PATENT DOCUMENTS

| JP | 2004-130262 | 4/2004 |
| KR | 2003-0019158 | 3/2003 |
| KR | 20-0313724 | 5/2003 |

OTHER PUBLICATIONS

Steinbrecher, Albert, "Electrolytic Production of Hydrogen Gas", Feb. 1939, Oil & Soap, pp. 36-39.*

* cited by examiner

*Primary Examiner* — Harry D Wilkins, III
(74) *Attorney, Agent, or Firm* — Kusner & Jaffe

(57) ABSTRACT

The present invention provides an apparatus for manufacturing sterilized water, spraying apparatus thereof and capsule containing salt using therein, more particularly, comprises a container having a water receiver for accommodating water; at least one negative electrode having at least one negative electrode projection formed thereon in the water receiver; at least one positive electrode having at least one positive electrode projection formed thereon arranged to face the negative electrode projection in the water receiver; and a power supply for supplying electric current to the negative electrode and the positive electrode, thereby promptly manufacturing a large amount of sterilized water within a short time, and thus, enabling users to use for disinfecting and sterilization the fresh sterilized water immediately after directly manufacturing the sterilized water without having aseptic to injured area or the inside of a nose for rhinitis' patients.

17 Claims, 15 Drawing Sheets

(a)

(b)

(c)

APPARATUS FOR MANUFACTURING STERILIZED WATER, AND PORTABLE APPARATUS FOR MANUFACTURING STERILIZED SALT SOLUTION

FIELD OF THE INVENTION

The present invention relates to an apparatus for manufacturing sterilized water, spraying apparatus thereof, and capsule containing salt using therein, more particularly, to such an apparatus for manufacturing sterilized water using oxidants generated by more vigorous electrolysis within a short time, a spraying apparatus and a capsule containing salt for sterilizing and cleansing a injured area or nose of rhinitis' patients with a portable type thereof.

BACKGROUND OF THE INVENTION

As is well known, environmental diseases have been increased as air and soil pollution has been deteriorated, and the concern for a well-being and health has been increased. Accordingly, rhinitis' patients washing their noses with a normal saline in the market have been increased.

On the other hand, a normal saline solution is generally manufactured by sterilizing a large amount of distilled water by heating water with high pressure for about 30 minutes, making saline water by putting sodium chloride (NaCl) into sterilized distilled water and adding antiseptics to limit the propagation of bacteria such as dymed, solvate etc.

However, such antiseptics have a risk to cause an allergy to rhinitis' patients so that rhinitis' patient using a normal saline purchased in a market is in danger of having an allergy. Also, a normal saline has been packed in a relatively big size over 1 l in order to satisfy the consumer's convenience and the proper packing cost. However, a normal saline packed in such a big package get easily contaminated after opening its package. In order to use fresh NS, user should use it up within 3~4 days after opening the package. In spite of the importance of uncontaminated condition of a normal saline, users go on using it after passing 3~4 days without discarding the rest of a normal saline. As a result, user can be easily exposed to other germs.

Therefore, in order for user's health and safety, needs for an apparatus for manufacturing sterilized water which users personally make and use a normal saline with user's convenience and using a normal saline directly after manufacturing it have been increased.

DETAILED DESCRIPTION OF THE INVENTION

Objects of the Invention

These disadvantages of the prior art are overcome by the present invention. It is an object of the present invention to provide an apparatus for manufacturing sterilized water using oxidants generated by more vigorous electrolysis within a short time.

Another object of the present invention is to manufacture the sterilized water wherever or whenever users want by providing the apparatus for manufacturing sterilized water with a portable size in order to carry it conveniently.

Still another object of the present invention is to provide a spraying apparatus for sterilizing and cleansing a injury region, an inflammation area or a nose of a rhinitis' patient directly after manufacturing the sterilized water within a short time at the consumer's level.

Yet another object of the present invention is to prevent the use of antiseptics needed for keeping a normal saline (i.e., isotonic salt solution) for a long time and to remove various problems in advance caused by the use of a contaminated normal saline through the use of a fresh normal saline made on the spot.

Still another object of the present invention is to realize the function of the spraying apparatus for sterilized water with a simple structure whereby the spraying apparatus is manufactured in a compact size and, therefore can be used everywhere.

Still another object of the present invention is to provide a saline solution capsule packed the proper amount needed for the normal saline of the spraying apparatus for sterilized water and a salt capsule using thereof.

SUMMARY OF THE INVENTION

In order to attain the above mentioned object, the present invention provides an apparatus for manufacturing sterilized water comprising: a container having a water receiver for accommodating water; at least one negative electrode in the water receiver; at least one positive electrode facing the negative electrode in the water receiver; and a power supply for supplying the electric current to both electrodes, wherein at least one negative electrode projection is formed on the negative electrode and at least one positive electrode projection facing the negative electrode projection is formed on the positive electrode.

This is to induct more vigorous electrolysis between the negative electrode projections and positive electrode projections confronting each other by making electric charges converge on the negative electrode projection(s) and the positive electrode projection(s) in the condition that the electric current is supplied to the negative electrode and the positive electrode. Here, it is desirable for the projections to be formed as plural.

After the electric power is supplied to the negative electrode projections and the positive electrode projections posed apart therefrom by a distance, the water between the negative electrode projections and the positive electrode projections is electrolyzed. Here, oxidants $O_3$, $H_2O_2$, OH radicals, HOCl are generated and sterilize microbes, viruses, fungus and bacteria. The oxidant formation and sterilizing process by electrolysis are realized by following (1) to (5) procedures.

(1) The process of ozone creation starts from electrolysis of $H_2O$ and finished with a combination of O and $O_2$.

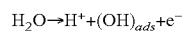
$H_2O \rightarrow H^+ + (OH)_{ads} + e^-$

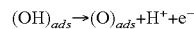
$(OH)_{ads} \rightarrow (O)_{ads} + H^+ + e^-$

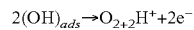
$2(OH)_{ads} \rightarrow O_2 + 2H^+ + 2e^-$

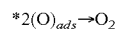
$*2(O)_{ads} \rightarrow O_2$

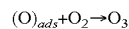
$(O)_{ads} + O_2 \rightarrow O_3$ (2) $H_2O_2$ is made by a direct process of electrolysis of $O_2$ and indirect process of a combination of OH radicals, a medium generated by $O_3$. That is, direct course,

$O_2 + e^- \rightarrow O_2^-$

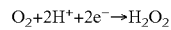
$O_2 + 2H^+ + 2e^- \rightarrow H_2O_2$

Indirect course,

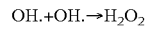
$OH \cdot + OH \cdot \rightarrow H_2O_2$ (3) HOCl is formed by chemical reaction with $H_2O$ after combining with $Cl^-$ existing in water with $Cl_2$.

$$2Cl^- \rightarrow Cl_2 + 2e^-$$

$$2H_2O + 2e^- \rightarrow H_2 + 2OH^-$$

$$Cl_2 + H_2O \rightarrow HOCl + H^+ + Cl^-$$

(4) OH radicals are created and vanished too soon to measure it directly, but in the case of ozone existing in water, OH radicals are finally created forming radical chain cycle with reacting with $HO2^-$, conjugate base of $H_2O_2$, or $Oh^-$.

$$O_3 + OH \rightarrow \text{Radical Chain Reaction} \rightarrow OH.$$

$$O_3 + HO^{2-}(\text{conjugate base of } H_2O_2 \rightarrow \text{Radical Chain Reaction} \rightarrow OH.$$

(5) Microorganisms existing in water get removed or inactivated by the oxidants, the following microorganism is removed by electroadsorption and the following microorganics gets removed by direct electrolysis reacting with $e^-$.

That is, regarding the microorganism, $$M(\text{Microorganism}) \rightarrow \text{Electrosorption} \rightarrow \text{Inactivation}$$

Also, $$M(\text{Microorganism}) + O_3 \rightarrow \text{Inactivation}$$

$$M + OH. \rightarrow \text{Inactivation}$$

$$M + HOCl \rightarrow \text{Inactivation}$$

And, regarding microorganics, $$M(\text{Microorganics}) + e^- \rightarrow M-$$

Also, $$M(\text{Microorganics}) + O_3 \rightarrow \text{Product}$$

$$M + OH. \rightarrow \text{Product}$$

$$M + HOCl \rightarrow \text{Product}$$

That is, during electrolysis, oxidation or sterilization is actively performed by the various oxidants ($O_3$, $H_2O_2$, HOCl, OH radicals) formed in the (1) to (5) procedures and, after the electrolysis, the sterilizing process can last due to the high residency characteristics of HOCl so that all the viruses including H5N1, HPV (Human Papillomavirus) causing a cervix cancer and fungi can be sterilized.

Here, $H_2O_2$ generated in the procedure of electrolysis can make free radicals, HO.+O. and these free radicals decompose proteins into peptide and amino acid with low molecular weight so that protein turns into water-soluble substance and converges on a double-bonded area, and epoxide is formed. (For instance, C=C—R become C—C—R) More specifically, free radicals formed in $H_2O_2$ have high reactivity and attacks other organic molecules like protein for stability of itself hereby oxidization of $H_2O_2$ decomposes protein into amino acid, water-soluble substance and remove protein, one of causes for allergies.

Herein, the negative electrode and the positive electrode form a plate shape, on which projections shaped like a cylindrical pillar or having its acute end are formed respectively to face each other, so that more electric charges can be concentrated on the end of the projections, and thus, electrolysis can be more prompted. Also, in order to induct more vigorous electrolysis in the unit area, it is preferable that the negative electrode and the positive electrode form plural pairs of plates or rods.

On the other hand, branch plates ramified from the respective surfaces of the plate-shaped negative electrode and the plate-shaped positive electrode projects, and the branch plate ramified from the negative electrode and the branch plate ramified from the positive electrode are arranged to face each other one by one, and further, the negative electrode projections and the positive electrode projections are respectively formed in the facing branch plates whereby electrolysis area can be maximized in the minimum space. Furthermore, additional branch plate can be formed from the branch plate, and negative electrode projections and positive electrode projections are formed in the facing side of the other branch plates extended from a negative electrode and a positive electrode.

Herein, in order to induct more vigorous electrolysis near the negative electrode projections and the positive electrode projections, it is desirable that the negative electrode projections and the positive electrode projections are made of platinum or plated with platinum. Here, platinum can cover the whole surface of the electrode, but it is more efficient to thickerly plate the only area which negative electrode projections and a positive electrode projections are formed than other parts.

Alternatively, grooves formed thereon instead of the positive electrode projections and the negative electrode projections can achieve the identical effect by causing electric charges to converge on the specific areas.

Also, if the negative electrode projections and the positive electrode projections are made of platinum and are formed as proper size, only the used-up projections can be replaced by screw connection. On the other hand, in order to reduce the manufacturing cost, the negative electrode projections and the positive electrode projections can be plated with titanium or be made of titanium or carbon.

In order to prevent the electrode from being damaged by an electric current flowed in the container without water, the present invention includes a sensor to monitor if the container has water in it or not.

Also, the apparatus according to the present invention further comprises a support having at least one negative slot to fix the negative electrode(s) and at least one positive slot to fix the positive electrode, which connect the cathode from the power supply with the negative slot (i.e., the negative electrode) and connect the anode from the power supply with the positive slot (i.e., the positive electrode). Therefore, the electrodes can be easily installed and replaced within the container just by inserting it into the slots of the support.

The water includes tap water, underground water. Further, saline water can be used in order to induct more vigorous electrolysis.

On the other hand, the present invention provides an apparatus for manufacturing sterilized water comprising: a pipe; at least one negative electrode having at least one negative electrode projection within the pipe; at least one positive electrode having at least one positive electrode projection facing the negative electrode projection each other; and a power supply for supplying the electric current to the negative electrode and the positive electrode.

This is to promptly and directly disinfect and sterilize flowing water in the pipe by supplying the electric current to the negative electrode and the positive electrode within the pipe. In this regard, it is desirable for the negative electrode and the positive electrode to be formed as long enough to fully sterilize the water fully following the pipe.

On the other hand, the present invention provides an apparatus for spraying sterilized water: comprising a container for accommodating the water; at least one electrode unit installed for sterilizing the water in a place where the water passes through including a negative electrode and a positive electrode facing the negative electrode apart therefrom; a power supply for supplying the electric current to the electrode unit; and a supplier for supplying water from inside of the container to outside.

This is to sterilize or wash inflammation areas, wound areas or inside area of a nose by conveniently spraying sterilized water immediately after manufacturing the sterilized water. Therefore, a user does not need to use the conventional method of spraying the purchased sterilized water which had been manufactured long before in condition of high temperature and high pressure. Rather, the user can make sterilized water on the spot using oxidants generated by electrolysis within a short time. Therefore, various side effects caused by using contaminated water or a normal saline containing antiseptics can be prevented in advance, and the spraying apparatus with a simple structure can be manufactured in a compact size so that user can use the apparatus as a portable one.

Here, it is preferable to comprise a plurality of negative electrode projections formed in the negative electrode and positive electrode projections which are arranged facing the negative electrode projections. This causes more electric charges converge or be concentrated on the negative electrode projections and the positive electrode projections when the electric power is supplied to the negative electrode and the positive electrode so that the more vigorous electrolysis is inducted between both projections facing each other, and only small amount of the electric power is required to promptly manufacture the sterilized water. Further, as plural current paths separated apart from one another are formed between the positive projections and the negative projections whereby $Cl_2$ gas is distributedly generated with small amount at the respective current path. Therefore, $Cl_2$ gas is easily reacted with water $H_2O$ by increasing the contact area between $Cl_2$ gas and water $H_2O$ as described by the chemical equation in (3), and thus the generated amount of HOCl is maximized even when only low current is applied to the electrode.

Herein, the negative electrode and the positive electrode form a plate shape, on which projections shaped like a pillar or having its sharp end are formed respectively so as to face each other. Therefore, more electric charges can be concentrated on the end of the projections, and thus, electrolysis can be more prompted. Also, in order to induct more electrolysis in the unit area, it is preferable that the negative electrode and the positive electrode form plural pairs of plates or rods.

On the other hand, at least one branch plate ramified from the surface of the plate-shaped negative electrode and the plate-shaped positive electrode is protrudedly formed. Also, the branch plate ramified from the negative electrode and a branch plate from the positive electrode are arranged facing each other one by one, and further, the negative electrode projections and the positive electrode projections are respectively formed on the facing branch plates, whereby electrolysis area can be maximized in the minimum space. Furthermore, an additional branch plate can be formed from the branch plate, and negative electrode projections and positive electrode projections is also formed in the facing side of the other branch plates extended from a negative electrode and a positive electrode.

Herein, in order to induct more vigorous electrolysis near the negative electrode projections and the positive electrode projections, it is desirable that the negative electrode projections and the positive electrode projections are made of platinum or plated with platinum. Here, platinum can cover the whole electrode, but it is more efficient to thickly plate the area which negative electrode projections and a positive electrode projections are formed.

Alternatively, grooves instead of the projections can be formed to achieve the identical effects by causing electric charges to be concentrated on the specific areas.

Also, if the negative electrode projections and the positive electrode projections are made of platinum and are formed as proper size, projections can be easily replaced by screw connection. On the other hand, in order to reduce the manufacturing cost, the negative electrode projections and the positive electrode projections can be plated with titanium or be made of titanium.

Also, users can conveniently sterilize the water in the container by simply pressing a switch by further comprising a switch to supply the electric power for a preset time which is input when the apparatus is manufactured in a factory.

The electric power supply can be an AC power having voltage converter from AC power to DC power. However, for users' convenience, it is more desirable that the electric power supply is a battery which can be easily purchased in the market thereby realizing the apparatus as a portable one. Herein, rechargeable battery is more desirable.

On the other hand, the container can form a big chamber for accommodating large amount of water, and the spraying apparatus can be supplied to users with a special pump according to user's needs. That is, such container of a big size can be used in a hospital or a dental clinic in order to sterilize or disinfect inside of a mouth or a injury region for curing. In such a big container, it is desirable that the bigger electrode is installed and the power is supplied to the electrode using AC power and converting it to the direct electric power by a transformer.

In order to discharge the heat of an electrode unit, at least one fin for discharging the heat is formed near the electrode, and a blowing fan to blow out the heat transmitted to the fin can also be comprised.

The spraying apparatus for spraying sterilized water comprises: a first chamber into which the water in the container can flow and in which at least one said electrode unit is installed; and a second chamber in which the power supply and the controller is installed, wherein the first chamber and the second chamber is divided by a partition in order to prevent the water in the first chamber from permeate into the second chamber. With this constructions, the water in the container flowed into the first chamber for being sterilized by oxidants generated in the electrode unit. As the power supply and the controller of the second chamber should be waterproof, a rubber ring is formed in the circumference of the partition.

Also, a circulation fan is installed within the first chamber for circulating water between the first chamber and the container, thereby prompting the circulation of the sterilized water near the electrode. Herein, it is effective for the circulation fan to operate only when the electric power is supplied to the electrode unit. Thus, it is possible to quickly sterilize the water as well as to maintain the inner area of the container to be an aseptic condition.

Also, the present invention includes a support having at least one negative slot to fix the negative electrode(s) and at least one positive slot to fix the positive electrode(s) and connecting the cathode from the power supply with the negative slot and the anode from the power supply with the positive slot. Therefore, the electrodes can be easily installed and easily replaced in the container by inserting it into the slots of the support. And the electrode itself can be replaceable.

On the other hand, the electric power supply can reverse the direction of the electric current to be supplied to the electrode unit. For example, anode power is firstly supplied to the electrode unit working as a positive electrode, and then, after a specific period, the cathode power is changed to supplied to the second electrode unit working as a negative electrode, whereby it can prevent residues from adhering to the each surface of the electrode during electrolysis. The specific period can be preset as 1 to 10 times or as 2 to 5 days in advance or by the user's handling.

The apparatus can use one of tap water, underground water, distilled water and purified water. Further, in order to make more vigorous electrolysis, saline water can be used. In this regard, although it is desirable to use distilled water or purified water instead of using tap water having a little impurities, it is possible to directly use a tap water or underground water having a little impurities after filtering in the different container.

Further, when saline water is to be used therein, although normal saline purchased in the market can be used, the appropriate saline water can be manufactured by firstly filling tap water or distilled water in a container, secondly inserting the proper amount of highly concentrated saline solution into the water considering the amount of the water in the container, and then, mixing the water and the saline solution. Using NS of 0.5% to 5% salinity instead of water maximize the disinfect effects and quickly manufacture the sterilized water by more vigorous electrolysis. Herein, when normal saline purchased in the market is used, considering that it would be possible to cause a side effect such as an allergy to users, it is more effective to use fresh saline water manufactured on the spot by mixing tap water with the highly concentrated saline solution or salt powder.

On the other hand, the present invention provides a salt capsule and a saline solution capsule which packs a saline solution or a salt in order to easily manufacture the desired salinity of saline water when using the spray apparatus for spraying sterilized water. This is to make sterilize water conveniently and easily everywhere users need it only by carrying small sized salt capsules or salt amples instead of a normal saline of 0.9% salinity.

Herein, the packed amount of saline water of salt in the capsule is for manufacturing water in the apparatus to be salt solution having 0.5% to 5.0% salinity, more desirably as having about 0.9% salinity which has the best sterilizing effect for the nose of rhinitis' patient. Therefore, users simply can make saline water having 0.9% salinity just inserting the content (i.e., salt powder or highly concentrated salt solution) in the capsule into the container. Here, the saline solution can be used by saturated saline solution, but it is more desirable to use a saline solution as having proper salinity according to the amount of water in the container.

On the other hand, the present invention provides a water filter comprising a filter for filtering the impurities of tap water or underground water in order to use the purified water for the container.

The Advantageous Effects of the Invention

As explained above, the present invention provides an apparatus for manufacturing sterilized water comprising: a container having a water receiver for accommodating water; at least one negative electrode in the water receiver; at least one positive electrode facing the negative electrode in the water receiver; and a power supply for supplying the electric current to both electrodes, wherein at least one negative electrode projection is formed on the negative electrode and at least one positive electrode projection facing the negative electrode projection is formed on the positive electrode, whereby it sterilize viruses and bacteria in a short time using oxidants generated by the more vigorous electrolysis between the negative electrode projection and the positive electrode projection.

As the apparatus for manufacturing sterilized water in accordance with the present invention can make sterilized water in 2~3 minutes using potable water such as tap water, underground water, it can be used everywhere the potable water is.

Also, the apparatus for manufacturing sterilized water in accordance with the present invention has a simple structure so that it can reduce manufacturing cost and can be manufactured in a portable type. Therefore, the apparatus for manufacturing sterilized water in accordance with the present invention can be used regardless of a place and for various usages such as lens washing, mouth sterilization, nose disinfection etc.

Also, the apparatus for manufacturing sterilized water uses a principle that electric charges converge on the projections such as negative electrode projections and the positive electrode projections, thereby, shortening the manufacturing time of the sterilized water, and realizing to manufacture the sterilized water only with small amount of electric power.

Also, as explained above, the present invention provides an apparatus for spraying sterilized water which can immediately spray the sterilizing water inside of a nose or a injured area right after manufacturing the sterilized water, which comprises: a container for accommodating the water; at least one electrode unit installed for sterilizing the water in a place where the water can flow into including a negative electrode and a positive electrode facing the negative electrode apart therefrom; a power supply for supplying the electric current to the electrode unit; and a spray for spraying water from inside of the container to outside, whereby lots of oxidants are created in a short time in the electrolysis, and the oxidants sterilizes and disinfects the water in the container, and then, users can immediately spray the sterilized water to places where users want.

That is, users can sterilize a nose or a wound region using sterilized water which does not contain antiseptics at any rate, and can use uncontaminated fresh sterilized water immediately after manufacturing it.

While the conventional sterilizing apparatus requires a big sized equipment for doing process of high temperature and high pressure, the apparatus according to the present invention sterilize and disinfect water by electrolysis caused by supplying electric power to the electrode unit, whereby right after user's direct manufacturing the sterilized water, the users can directly spraying or supplying the sterilized water to where the users wish to spray, such as an inflammation area, a wound area, or an inside area of a nose. Therefore, various side effects caused by using contaminated water or a normal saline containing antiseptics can be prevented in advance. Further, the spraying apparatus with a simple structure can be manufactured in a compact size so that user can carry it easily as a portable one.

Here, as negative electrode projections and positive electrode projections are formed in the negative electrode and the positive electrode to face each other, the electrolysis can be realized more vigorously so that many oxidants are generated within a very short time, and further, they sterilize and disinfect viruses and bacteria effectively. Also, as the electric charges converged on each electrode projections, only small sized battery can be used adequately for disinfecting and sterilizing the water.

Also, as the apparatus for spraying sterilized water in accordance with the present invention uses any type of potable water such as tap water, underground water and make normal saline (i.e., isotonic saline solution) with 0.75% to 1% salinity by mixing highly concentrated saline solution having the proper salinity with the water, it can make sterilized water with various salinities appropriate for the spraying area.

Also, the apparatus for spraying sterilized water in accordance with the present invention has a simple structure so that it can reduce manufacturing cost and can be manufactured in a compact size.

On the other hand, in order to manufacture saline water used for the apparatus for spraying sterilized water, the present invention provides a saline solution capsule and a salt capsule whereby user can simply make sterilized water with about 0.9% salinity, just by putting salt in the capsule into the water in the apparatus thereby making users manufacture normal saline everywhere and at any time.

Embodiments

BRIEF DESCRIPTION OF THE DRAWINGS

Accordingly, the present invention will be understood best through consideration of, and reference to, the following Figures, viewed in conjunction with the Detailed Description of the Preferred Embodiment referring thereto, in which like reference numbers throughout the various Figures designate like structure and in which.

DETAILED DESCRIPTION OF PREFERRED EMBODIMENTS

The foregoing and other objects, features, aspects and advantages of the present invention will become more apparent from the following detailed description of the present invention when taken in conjunction with the accompanying drawings.

In describing the present invention, detailed description of laid-out function or structure is omitted in order to clarify the gist of the present invention.

Figure 1:
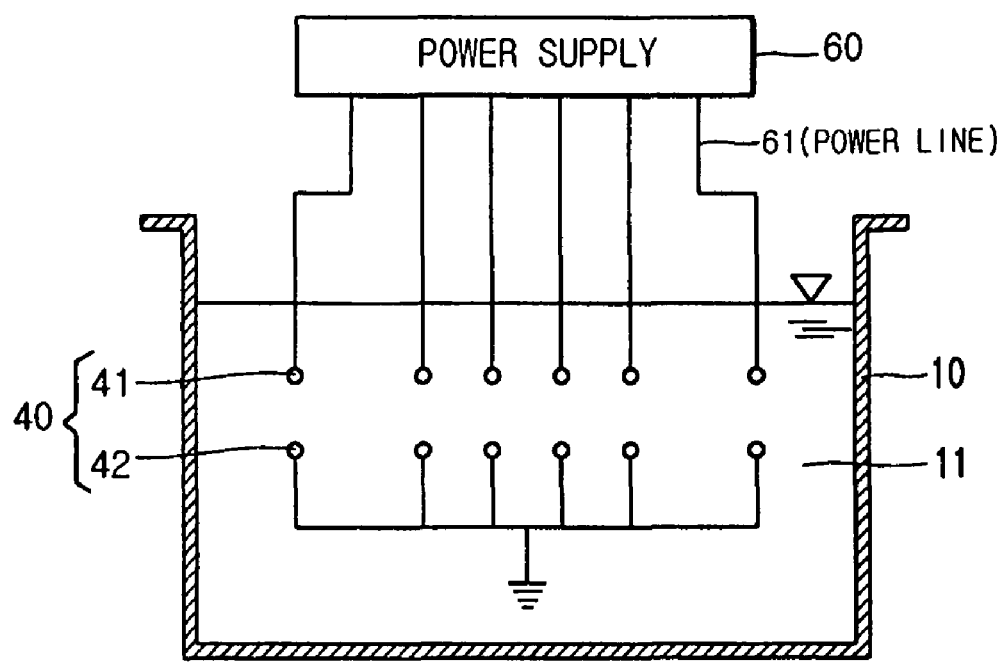
FIG. 1 is a diagram showing a principle of an apparatus for manufacturing sterilized water in accordance with the present invention.

As shown in FIG. 1, the present invention uses a principle that which installs the positive electrode 41 and the negative electrode 42 apart therefrom within the water 11 of the container 10, and, inducts electrolysis in the water by receiving the electric power through the electric power line 61 from an electric power supply 60 and sterilizes bacteria and viruses using oxidants like ozone, HOCl, OH radicals generated by the electrolysis.

Figure 2:
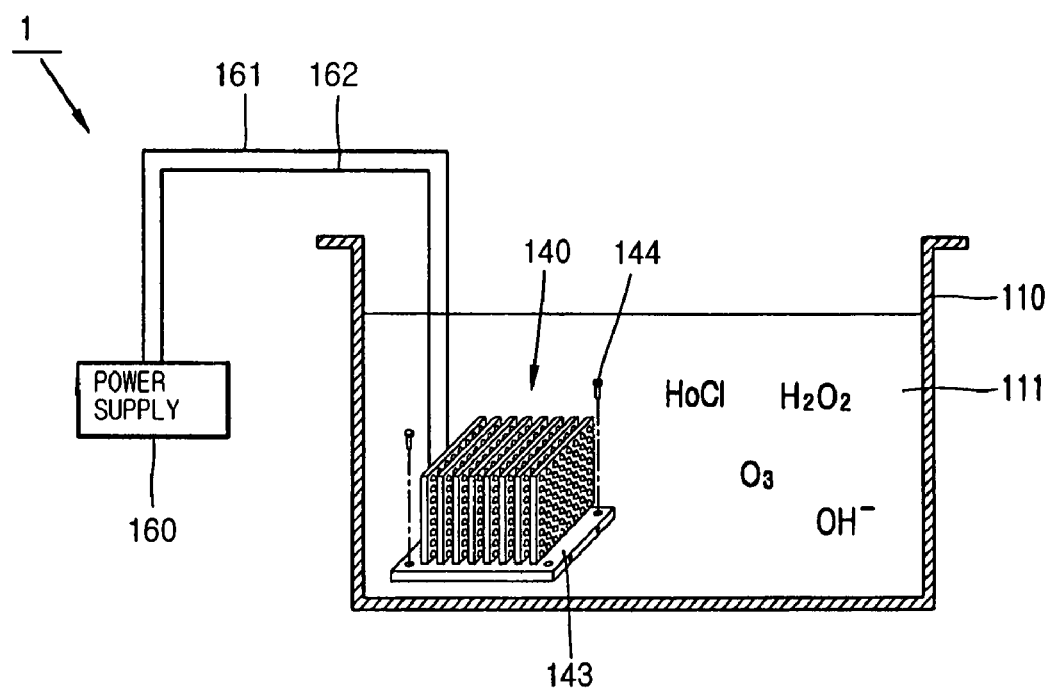
FIG. 2 is a diagrammatic representation of a structure of the apparatus for manufacturing sterilized water in accordance with one embodiment of the present invention.

The apparatus for manufacturing sterilized water 100, as shown in FIG. 2, comprises a container 110 for accommodating water 111, several electrode units 140 fixed to the ground of the container 110, and a power supply 160 for supplying the electric power to the electrode unit 140.

The container 110 forms reinforced plastics not to be damaged from outside shocks and includes a sensor (not shown) to monitor if the container 110 has water in its inside where the electrode unit 140 is installed.

The power supply 160 can use DC power converted from AC power or DC power supplied from at least one battery. A cathode line 161 from the power supply 160 is connected to a negative electrode plate 141, and an anode line 162 from the power supply 160 is connected to a positive electrode plate 142.

Figure 3:
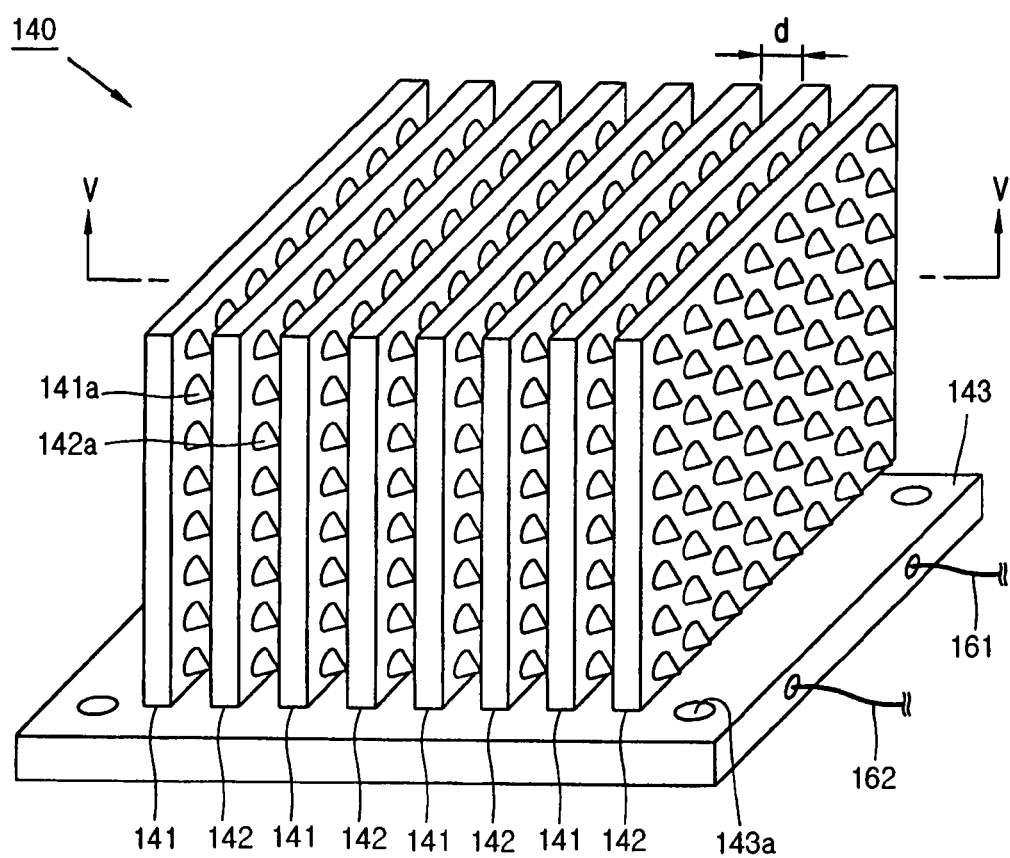
FIG. 3 is a perspective view illustrating a structure of an electrode in FIG. 2.
Figure 4:
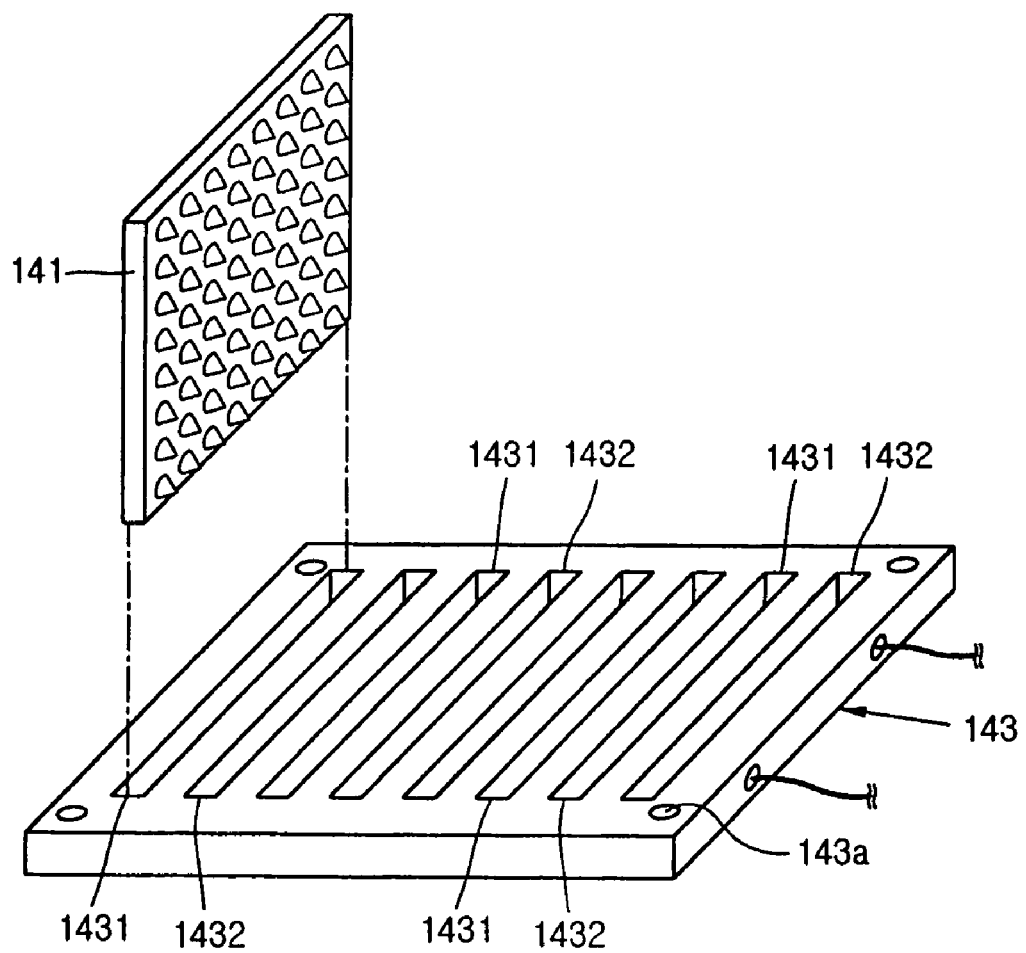
FIG. 4 is an exploded view of FIG. 3.
Figure 5:
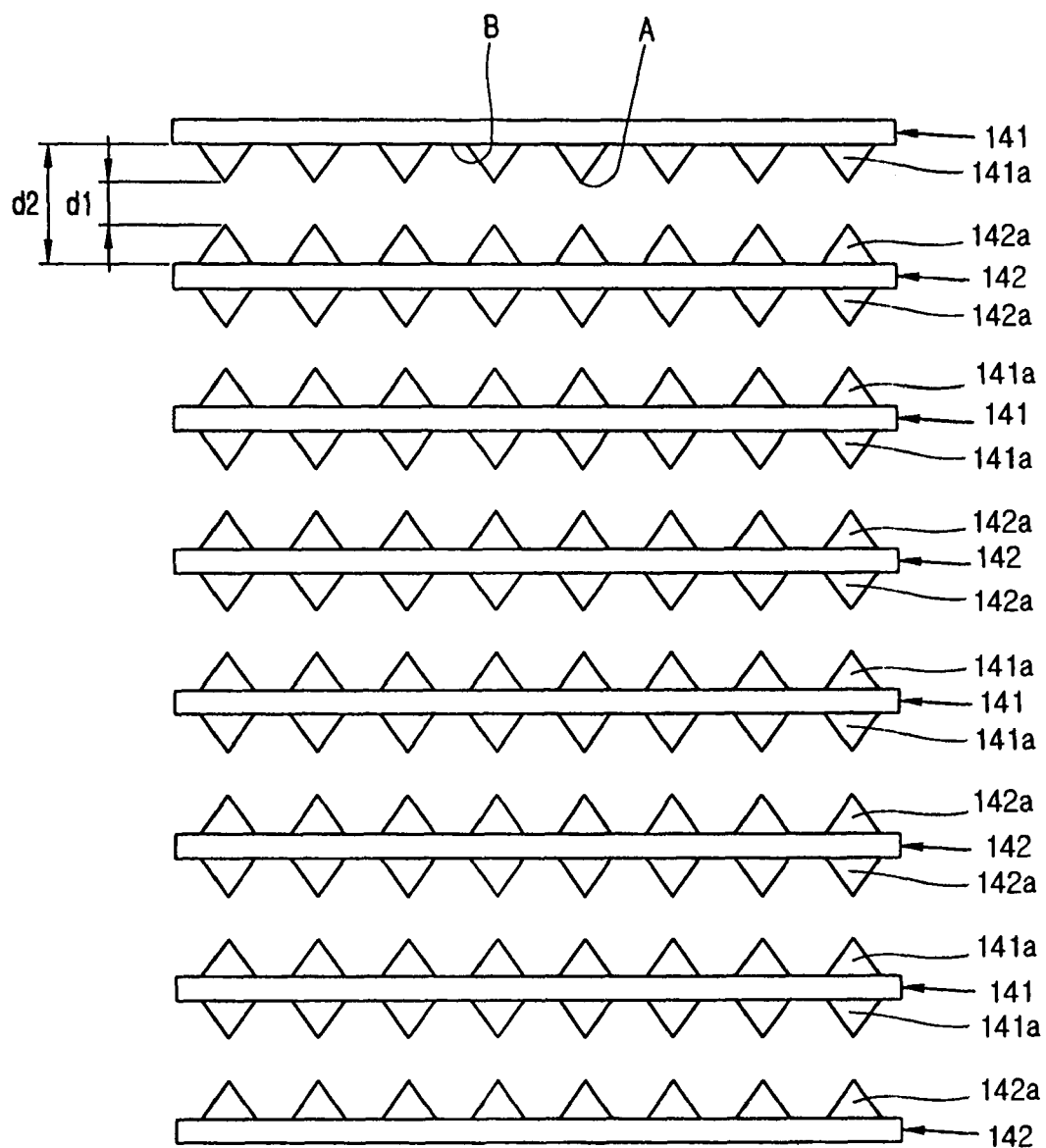
FIG. 5 is a cross-sectional view by cut line V-V in FIG. 4.

The electrode unit 140, as illustrated in FIGS. 3 to 5, includes a negative electrode plate 141 having plural negative electrode projections 141a on its surface, a positive electrode plate 142 having plural positive electrode projections 142a on its surface, a support 143 fixed to the ground of the container 100 so as to fix the negative electrode plate 141 and the positive electrode plate 142, and a fixing screw to fix to the ground of the container passing through a fixing hole 143a of the support 143.

Here, the negative electrode plate 141 and the positive electrode plate 142 is fixed to the support 132 where the plates 141, 142 are apart from each other at a distance d2. Moreover, the negative electrode 141 and the positive electrode 142 are fixed to the support 132. The negative electrode projection 141a and the positive electrode projections 142s are protuberantly formed on the surface B of the negative electrode 141 and the positive electrode 142 respectively so as to face each other, whereby the electric charges supplied to the electrode plates 141, 142 are converged on the fore-end of the projections 141a, 142a and prompt the electrolysis between the negative electrode projections 141a and the positive electrode projections 142a.

Also, the negative electrode projections 141a and the positive electrode projections 142a are thickerly plated with platinum so that the electrolysis is more actively generated.

Figure 6:
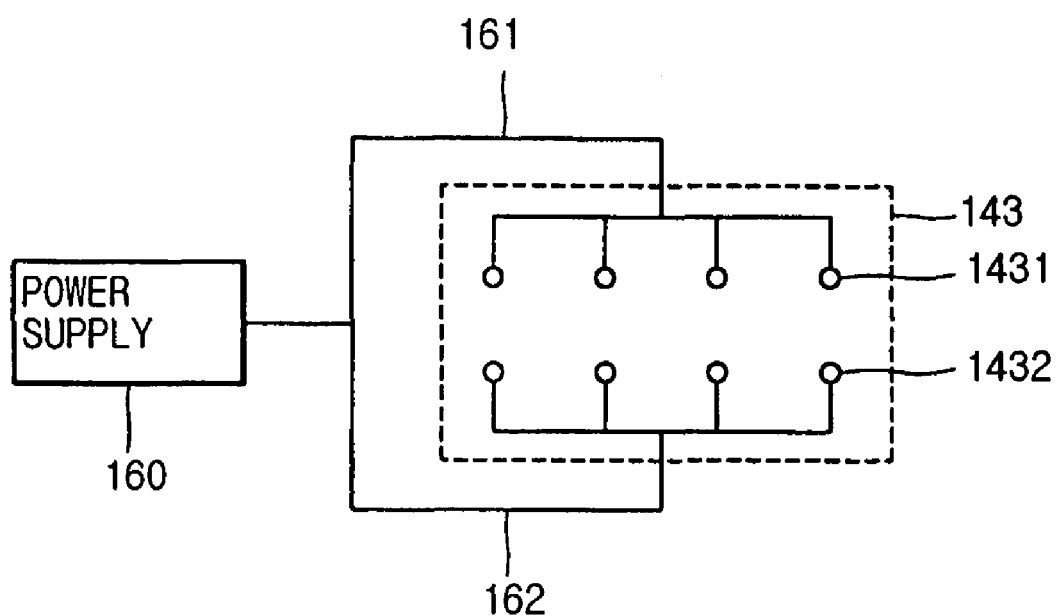
FIG. 6 is a wiring diagram illustrating power supply to an electrode of FIG. 2.

As illustrated in FIG. 4, the support 143 includes a connection slot 1431 formed concavely for fixing the negative electrode plate 141 and a connection slot 1432 formed concavely for fixing the positive electrode plate 142. As illustrated in FIG. 6, inside of the support 143, the cathode line 161 is connected to the connection slot 1431 for the negative electrode plate 141 and the anode line is connected to the connection slot 1432 of the positive electrode plate so that electric current can be supplied to the electrode plates 141, 142 just by inserting the electrode plates 141, 142 into the slots 1431, 1432 of the support 143.

Therefore, when the platinum of the electrode plates 141, 142 is used up, the replacement can be achieved just by separating the used electrode plates 141, 142 from the support 143, and thereafter, by inserting the new electrode plates into the slots 1431, 1432. Therefore, structured as above, the apparatus for manufacturing sterilized water can be used permanently.

Hereinafter, the operation principle of the apparatus for manufacturing sterilized water 100 in accordance with one embodiment of the present invention will be understood.

In the case of manufacturing sterilized water using the apparatus for manufacturing sterilized water 100 in accordance with one embodiment of the present invention, users firstly put tap water 111 into the container 100, and supply the electric power from the power supply 160 to the electrode unit 140 by the power's supplying the connection slot 1431 of the negative electrode plate and the connection slot 1432 of the positive electrode plate. Then, as the cathode power is supplied to the negative electrode plate 141 and the anode power is supplied to the positive electrode plate 142 through each connection slot 1431, 1432. Here, although the power is supplied to the negative electrode plate 141 and the positive electrode plate 142 respectively, the electric charges converge on the negative electrode projections 141a and the positive electrode projections 142a formed in a facing side of the plates 141, 142. Therefore, the electrolysis between the projections 141a, 142a is actively occurred whereby many oxidants such as ozone, $H_2O_2$, HOCl, OH radicals are generated, sterilized viruses and bacteria in a short time, and accordingly users can easily make sterilized water.

The apparatus for manufacturing sterilized water in accordance with one embodiment of the present invention needs to install the electrode plates 141, 142 having the projections 141a, 142a in the container so that it can be designed to be a compact size for carrying easily. Although the controller can not be included in the apparatus, a timer for operating for preset time can be included.

Figure 7:
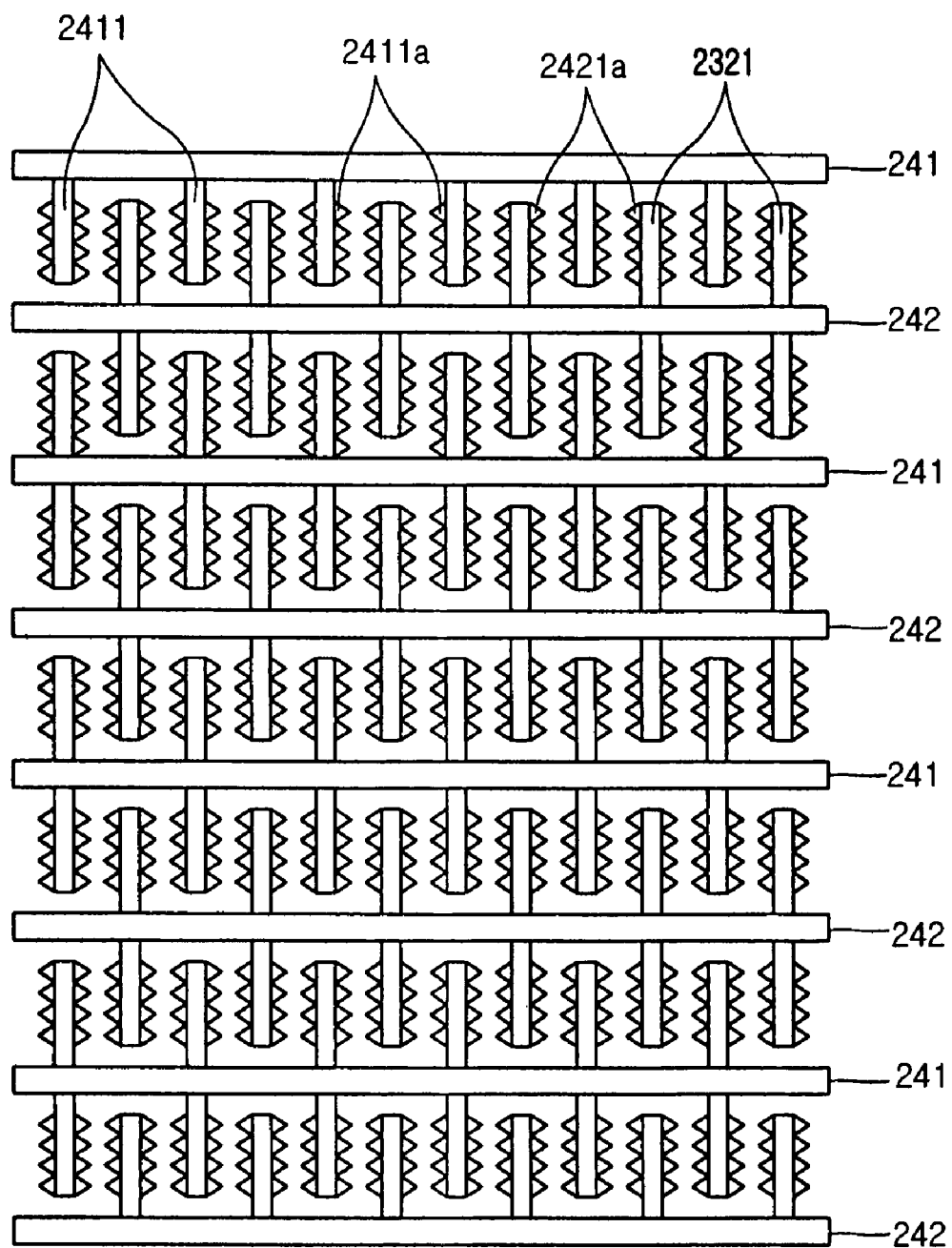
FIG. 7 is a cross-sectional view of the electrode structure in accordance with the second embodiment.

On the other hand, as shown in FIG. 7, a sectional view of the electrode of the apparatus for manufacturing sterilized water in accordance with the second embodiment, the electrode plates 241, 242 can include branch plates 2411, 2421 ramified from the plates 241, 242 and also have negative electrode projections 2411a and positive electrode projections 2421a formed on the branch plates 2411, 2421 facing each other at a nearer distance.

The structure as above can ensure the wide area of electrolysis in the predetermined area so that the sterilized water can be achieved within a shorter time.

Figure 8:
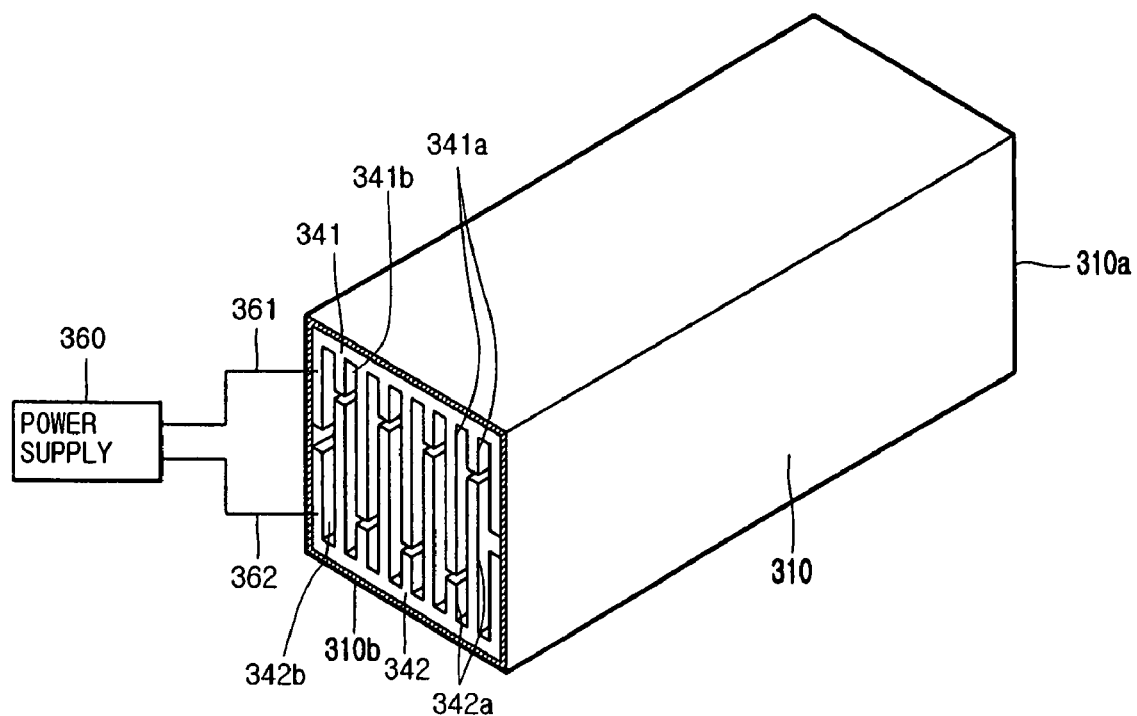
FIG. 8 is a diagrammatic representation of the electrode structure in accordance with the third embodiment.

FIG. 8 is a diagrammatic representation of the electrode structure in accordance with the third embodiment. The apparatus for manufacturing sterilized water in accordance with the third embodiment comprises: a pipe 310 formed for the passage of tap water or underground water; electrodes 341, 342 formed inside of the pipe 310; and a power supply 360 for supplying the electric power to the electrodes 341, 342.

One of the electrodes 341, 342 is connected with another pipe supplying water. For example, the pipe can be directly connected with a pipe supplying tap water, or the pipe also can be a pipe supplying tap water within which the electrodes 341, 342 are formed.

The electrodes 341, 342 comprise a negative electrode 341 supplied the electric power through the cathode line 361 from the power supply 360, and a positive electrode 342 supplied the electric power through the anode line 362 from the power supply 360. Here, negative electrode projections 341a are formed with different lengths in the negative electrode 341, and positive electrode projections 342a are protuberantly formed in the positive electrode 342 to face the negative electrode projections 341a so that the vigorous electrolysis is generated in the end of the negative electrode projections 341a and the end of the positive electrode projections 342a. The negative electrode projections (not shown) and the positive electrode projections (not shown) are also formed in the sides 341b, 342b of the facing projections of the negative electrode projections 341a and the positive electrode projections 342a, whereby the electric charges converged on the fore-end of these projections(not shown) can induct more active electrolysis.

That is, the apparatus for manufacturing sterilized water in accordance with the third embodiment have plural electrodes 341, 342 having negative electrode projections and positive electrode projections in the pipe's longitudinal direction. Therefore, when electric power is supplied to the electrodes 341, 342 during water's flowing in the pipe 310, as the water passing through the pipe 310 becomes turbulent flow, more contact area between the water and the electrodes 341, 342 is realized for more time, while the water passes through the pipe 310. Accordingly, the water pipe passing through the pipe 310 is vigorously electrolyzed so that the more oxidants can be created. As a result, the water passing through the pipe turns into sterilized water when the water is discharged from the pipe.

Figure 9:
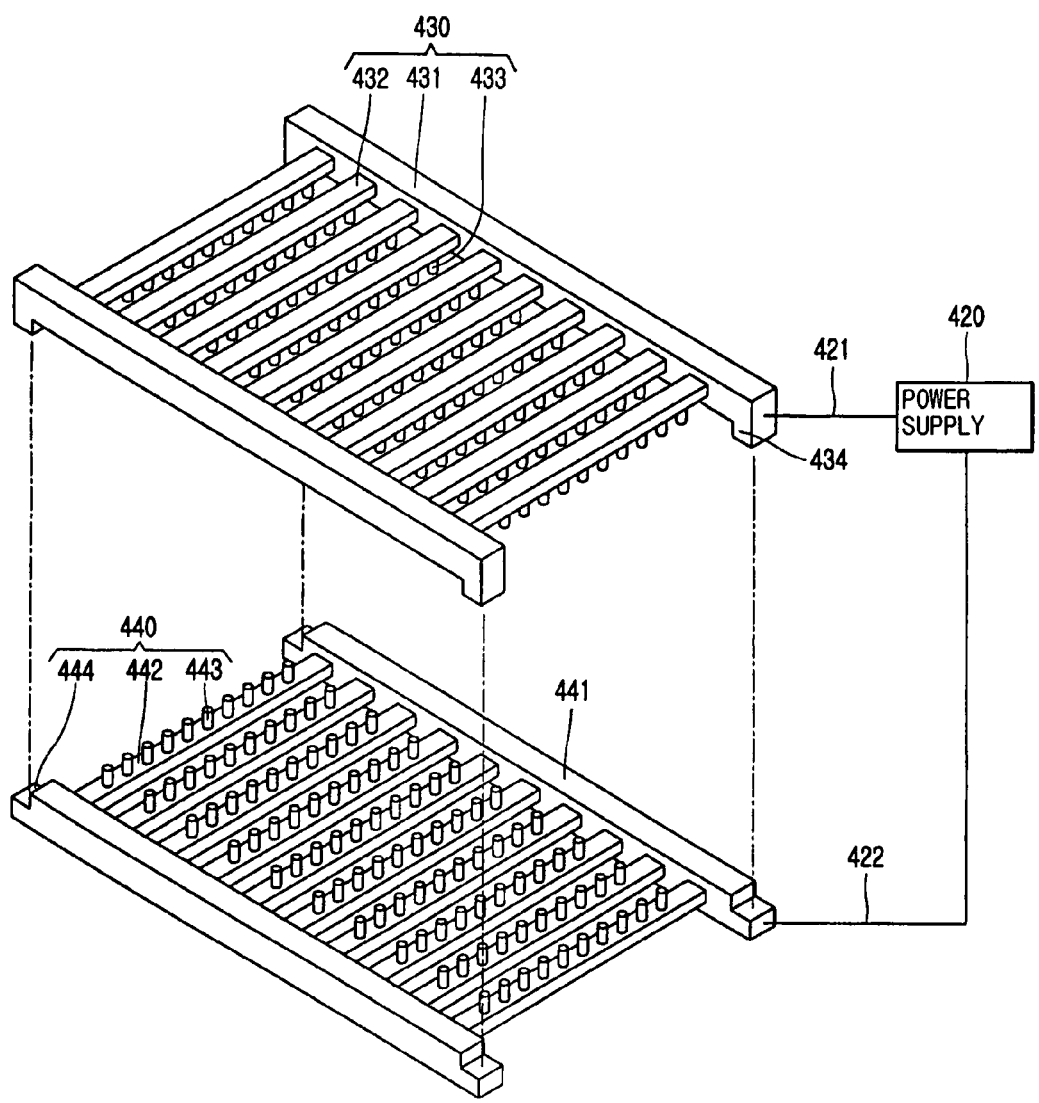
FIG. 9 is a cross-sectional view of the electrode structure in accordance with the fourth embodiment.

FIG. 9 is a cross-sectional view of the electrode structure in accordance with the fourth embodiment. As shown in FIG. 9, the apparatus for manufacturing sterilized water in accordance with the fourth embodiment has only a different electrodes' structure (i.e., electrodes 430, 440) compared with the above-described one embodiment 100 of the present invention. The apparatus comprises a negative electrode 430 to which the power supply 420 supplies the electric power through the cathode line 421, and a positive electrode 440 to which the power supply 420 supplies electric power through the anode line 422.

The negative electrode unit 430 includes a pair of negative support rods 431 formed of an electric conductor parallelly apart from each other and connected to a negative power line 421, a plurality of negative electrode rods 432 connecting between a pair of the negative support rods 431, the negative electrode projections 433 projected like a cylindrical pillar on the low side of the negative electrode rod 432 to concentrate electric charges thereon, and fitting protrusions 434 formed in the low side of the negative support rod 431 to ensure a predetermined distance from the positive electrode 440.

Similarly, the positive electrode unit 440 includes a pair of positive support rods 441 formed of an electric conductor parallelly apart from each other and connected to a positive power line 422, a plurality of negative electrode rods 442 connecting between a pair of the negative support rods 441, the positive electrode projections 443 projected like a cylindrical pillar on the upper side of the positive electrode rod 432 to concentrate electric charges thereon, and a fitting grooves 444 formed in the upper side of the positive support rod 441 to ensure the predetermined distance from the negative electrode 430.

In order to prevent the electric current from flowing between the negative electrode 430 and the positive electrode 440, an insulating pad is inserted between the fitting projections 434 and fitting grooves 444. Alternatively, the surfaces of the fitting projections 434 and fitting grooves 444 can be coated by insulation material. Also, when the projections 434 are fitted to the grooves 444 respectively, the fore-end of the negative electrode projections 433 keep a distance from the fore-end of the positive electrode projections 443 so that the vigorous electrolysis is inducted between them.

Structured as above, the electrodes 430, 440 of the apparatus for manufacturing sterilized water in accordance with the fourth embodiment has the electrode projections 433, 443 formed in the electrode rods 432, 442 so that it can be simply made by molding process, and that the loss of electric charges can be reduced, and that the cost for manufacturing the electrodes can be reduced.

Figure 10:
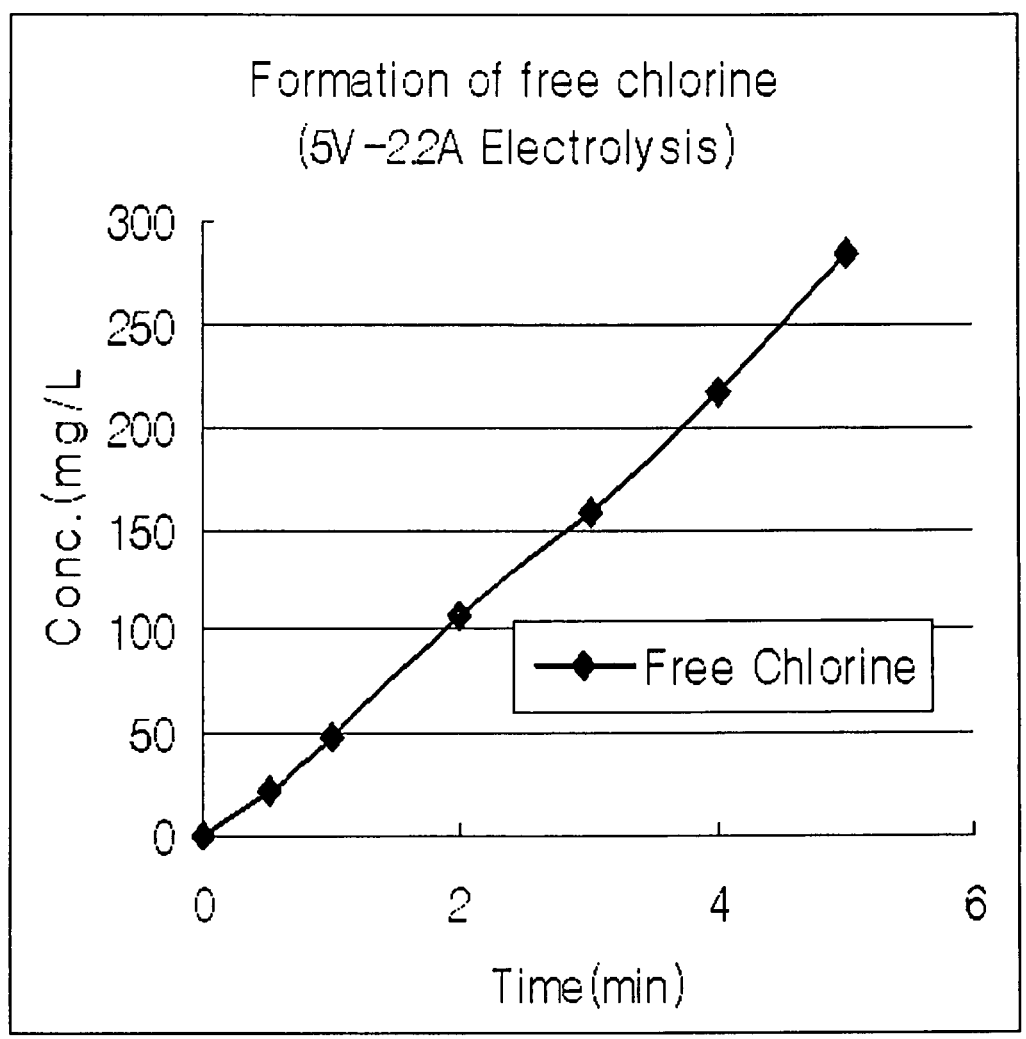
FIG. 10 is an experiment data graph illustrating measurement of chlorine ion increase in accordance with electrolysis of saline water.

FIG. 10 is an experiment data graph illustrating the increase of saline ion according to electrolysis by sending electric power of 5V, 2.2 A to the saline water having salinity 0.98% and pH 6.39. As shown in the experiment of FIG. 10, electrolysis is more active in the saline water so that the quick sterilizing effect can be achieved. Furthermore, projections 141a, 142a to converge more electric charges are formed in electrode plates 141, 142 whereby more active electrolysis than the experiment in FIG. 10 will be realized and the sterilizing time will be much more shorten. Therefore, the water used for the present invention can include saline water as well as tap water, distilled water.

Figure 11:
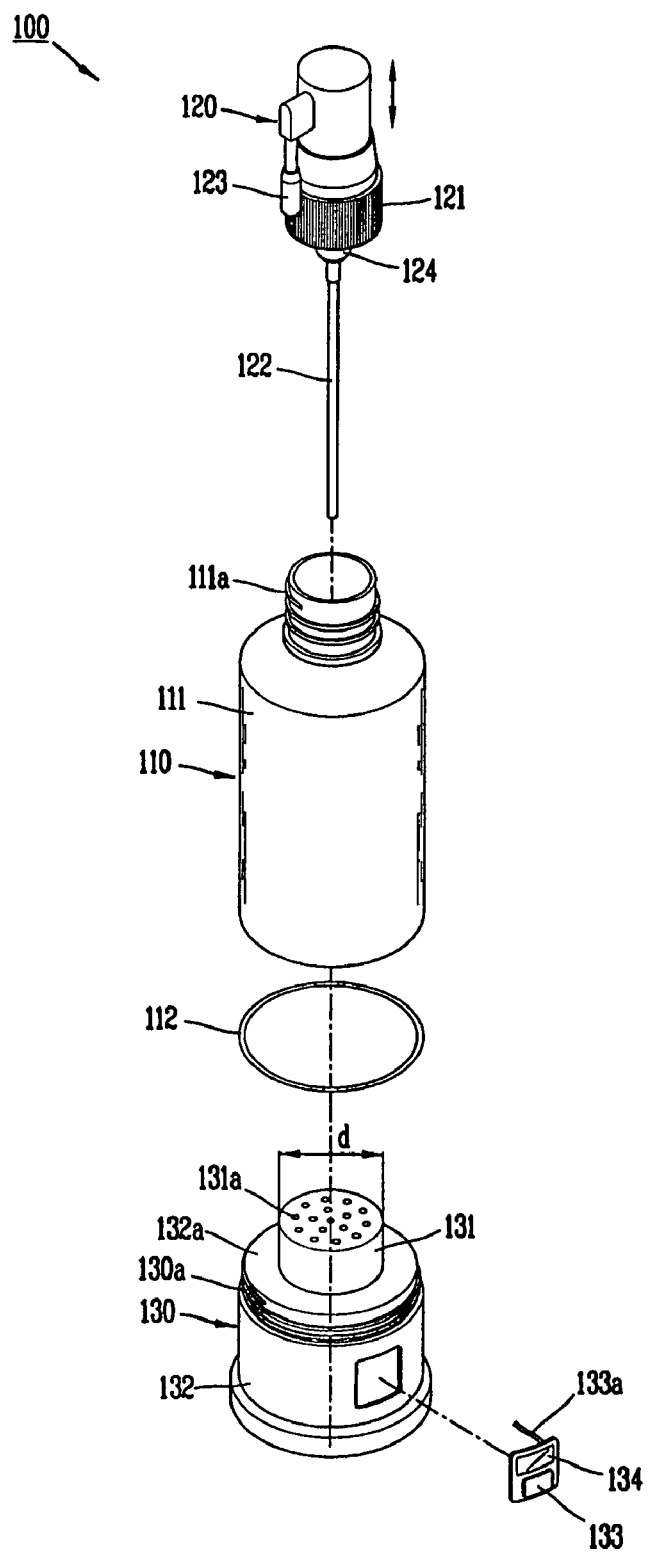
FIG. 11 is a dissembled perspective view of the apparatus for manufacturing sterilized water in accordance with the first embodiment of the present invention.
Figure 12:
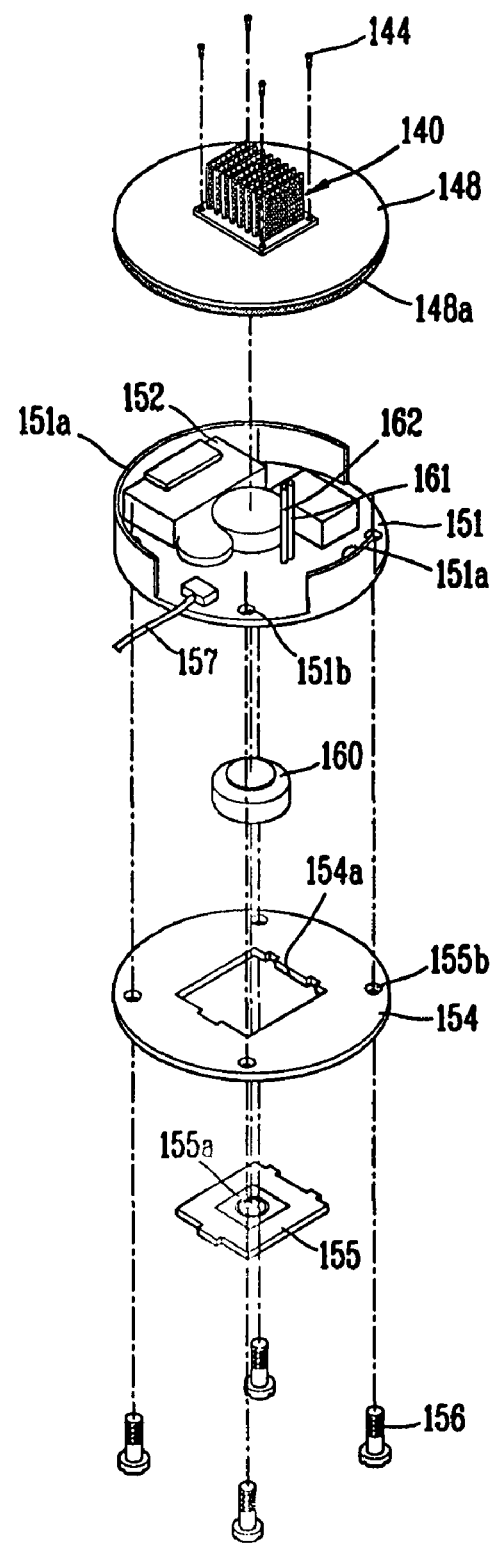
FIG. 12 is a dissembled perspective view of the electrode and the controller of FIG. 11
Figure 13:
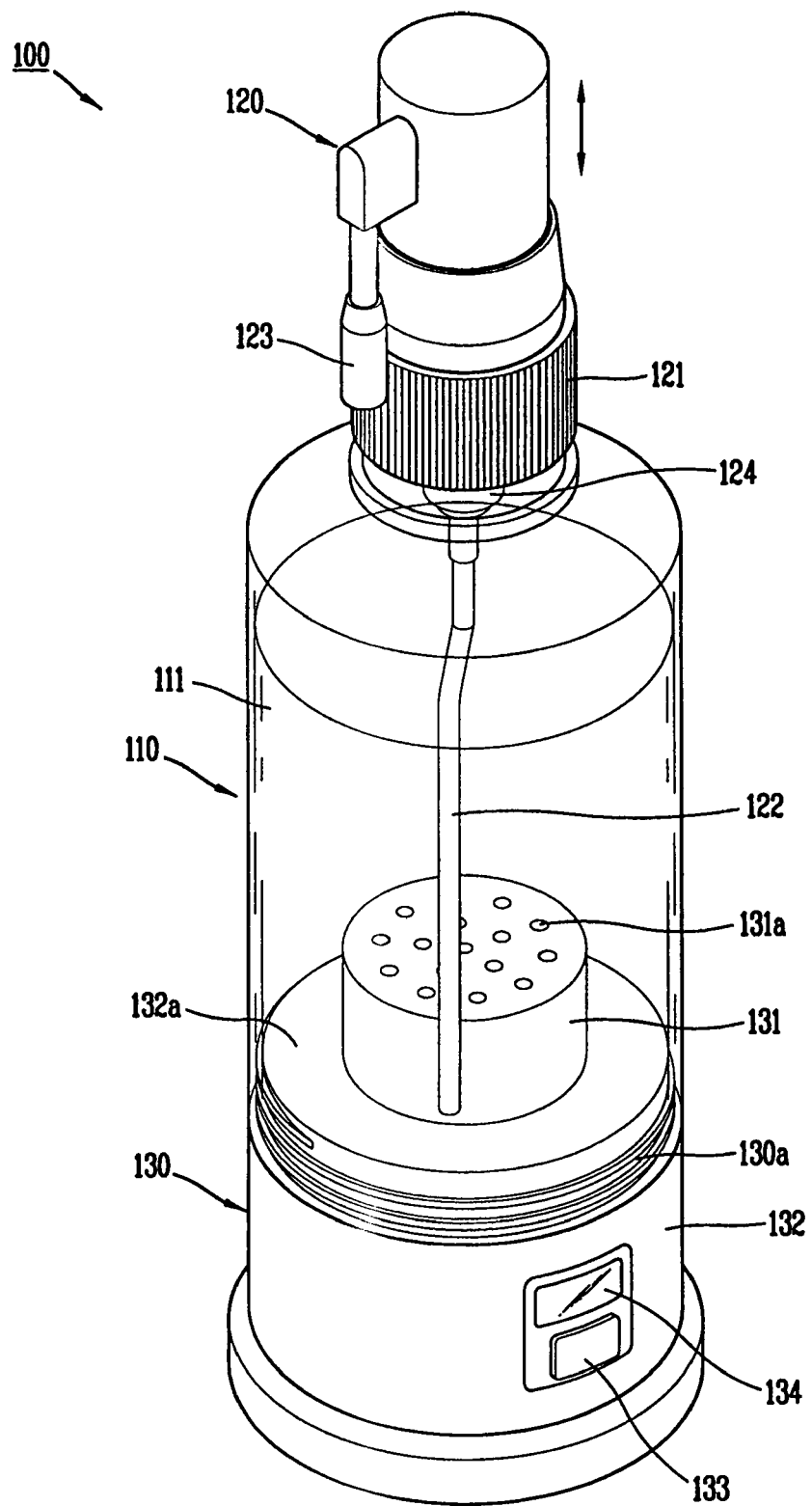
FIG. 13 is an assembled perspective view of FIG. 11.
Figure 14:
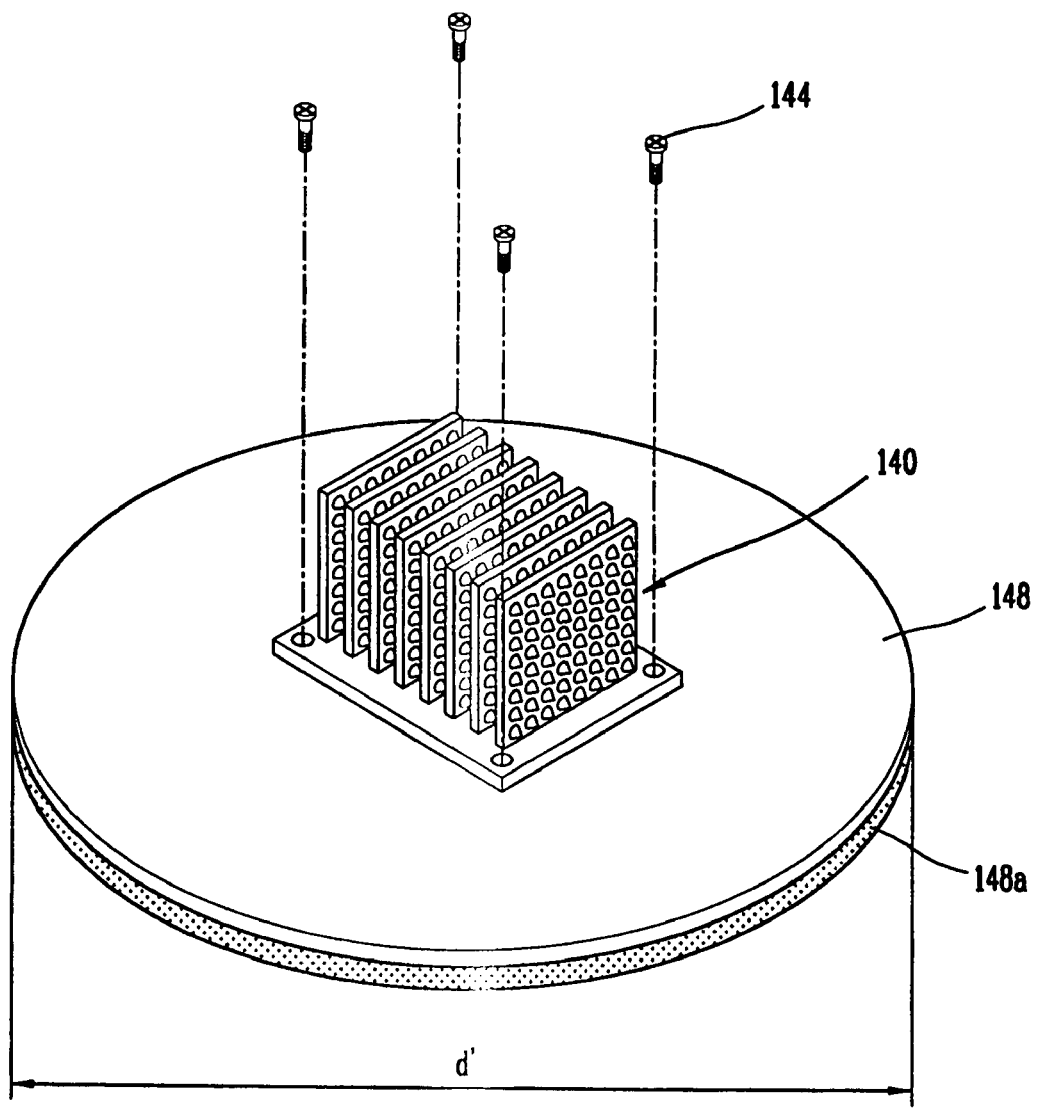
FIG. 14 is a perspective view of the electrode fixed on the partition of FIG. 12.
Figure 15:
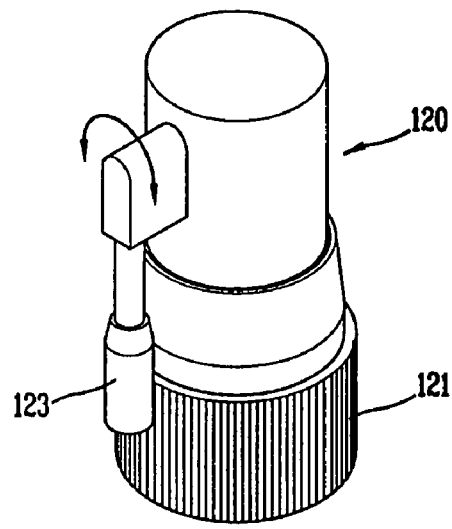
FIG. 15 is a drawing of the spray of FIG. 11.
Figure 15:
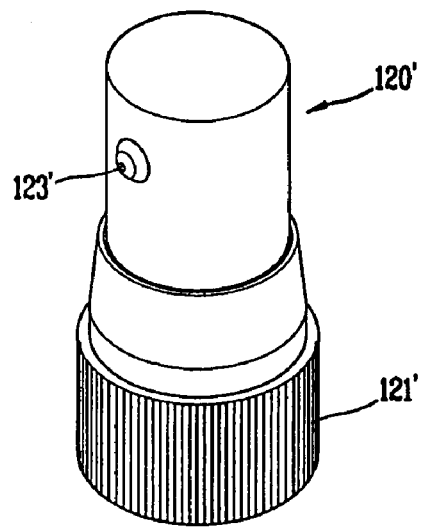
Figure 15:
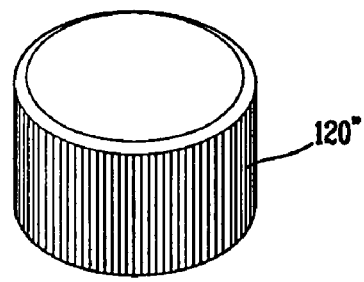

FIGS. 11 to 15 relate to the apparatus for manufacturing sterilized water in accordance with one embodiment. FIG. 11 is a dissembled perspective view of the apparatus for manufacturing sterilized water, FIG. 12 is a dissembled perspective view of the electrode and the controller of FIG. 11, FIG. 13 is an assembled perspective view of FIG. 11, FIG. 14 is a perspective view of the electrode fixed on the partition of FIG. 12, and FIG. 15 is a drawing of the spray of FIG. 11.

As shown in the figures, the apparatus for manufacturing sterilized water in accordance with one embodiment comprises: a container 110 for accommodating the water for manufacturing sterilized water; a spraying unit 120 for spraying the sterilized water to a wound area or inside of a nose; a body case 130 attachable to the low side of the container 110; several electrode units 140 within the body case 130 where the water in the container 110 can flow into for sterilizing the water; a controller 150 for controlling the electrode unit 140; and a power supply 160 for supplying the electric power to the electrode unit 140.

The container 110 includes a container 111 for accommodating water, and a ring 112 inserted with the low side of the container 111 for preventing water from leaking from the container 111 to the outside.

Here, if the injured area is facile to be contaminated by impurities, it is more desirable to use distilled water or purified water although the water can be tap water or underground water. Also, the tap water and underground water can be use after purifying them using an extra container having a filter. Here, saline water is desirable for the quick electrolysis and, moreover, has the best effect for sterilizing or washing the inside of a nose. Therefore, saline water having 0.75% to 1% salinity, more preferably 0.9% salinity is more preferable.

The spraying unit 120 includes a spray case 121 connected to a screw 111a formed in the upper side of the container 111, a spraying pipe 122 which is a passage of the sterilizing water in the vertical direction for spraying the sterilized water from inside of the container 111 to the outside, a spray 123 for spraying the sterilized water formed on the outer surface of the spray case 121, and a vacuum chamber 124 formed to generate a suction force to pump up the sterilized water from the container 111 to the outside.

Herein, in order to spray the sterilized water outside through the spraying unit 120, a user presses the apparatus to the direction of an arrow in FIG. 11, then the sterilized water is pumped up to the spraying unit 120 through the spraying pipe 122 by a instantaneous volume change of the vacuum chamber 124, and the sterilized water can be sprayed through the spraying unit 120 in a form of minute water drop. This structure is already laid out through various sprays.

The body case 130 is combined with a thread formed in the low side of a inner surface of the container 111, and includes a first chamber 131 for installing the electrode unit 140, the second chamber 132 for accommodating the controller 150 and the power supply 160 and an indicator 134 for showing the operation status.

Herein, the first chamber 131 is formed to enable the water in the container 110 to flow through the hollow 131a thereinto, and the second chamber 132 is formed separately from the first chamber in order for water not to permeate between the first chamber 131 and the second chamber 132.

When user presses the operation switch 133, the power is supplied to the electrode unit 140 for a preset time.

The electrode unit 140 is fixed to the partition 148 of the first chamber 131 with a fixing screw 144 and connected to the controller in order to be supplied the electric power or signals from the controller 150. Here, in order to connect between the electrode unit 140 and the power supplying rods 161, 162 of the controller, holes (no shown) are formed through the partition 148 in which the electrode unit 140 is posed. Also, a rubber packing 148a is attached in the circumference of the low side of the support 143 so that water cannot be permeate from the first chamber 131 to the second chamber through the holes.

Here, the rubber packing plate is formed in the low side of the partition 148, of which diameter is larger than the inner diameter of the first chamber 131, so that the rubber packing plate is tightly inserted into the inner surface of the first chamber 131 thereby preventing the water in the first chamber 131 from permeating into the second chamber 132. Therefore, a diameter d' of the partition 148 is a little bit smaller than the inside diameter d of the first chamber 131 so that the rubber packing plate 148a can realize water-proof. Herein, the rubber packing plate 148a can be formed as ring type to cover the edge portion of the partition 14 instead of being formed as a plate type. On the other hand, the electrode 140 can be formed as one of the electrodes 140, 240, 340 in FIGS. 3 to 9 which are already described, and also can be installed to be horizontally laid or vertically uprighted.

The controller 150 includes a control circuit fixing plate 151; a control circuit 152 for controlling the change of a power direction to supply the electric power to the electrode unit 140 according to the operation situation, for showing the operation condition by the indicator 134, and for supplying electric power to the electrode unit 140 for a preset time according to the input of the operation switch on the control circuit fixing plate 151; a battery receiver 153 for accommodating the battery 160 for supplying the electric power to the electrode unit 140; the low plate 154 fixed to the low side of the control circuit fixing plate 151; and a battery cover 155 to selectively close or open the hole 154a of the low plate 154.

Here, side wall 151a is uprightedly and protrudedly formed along the circumference of the control circuit fixing plate 151, and the upper surface (i.e., egde) of the side wall 151a gets in contact with the ceiling 132a of the second chamber 132 or the rubber packing 148a, thereby stably obtaining the second chamber 132 for installing the control circuit 152 between the control circuit fixing plate 151 and the partition 148. That is, the space between the ground of the control circuit fixing plate 151 and the upper side 132a of the second chamber 132 is prepared to fix the control circuit 152.

Then, by fastening the fixing bolt 156 to the fastening hole 151b of the control circuit fixing plate 151 through the hole 155b of the low plate 154, the installation of the controller 150 and the power supply 160 in the body case 130 is finished.

133a is a signal line connecting the controller 150, the operation switch 133, and the indicator 134. 155a is a metal plate to supply the power of the battery 160. An extra signal line from the metal plate 155a is connected to the controller 150.

The power supply 160 includes a battery 160, a positive electrode power rod 161 and a negative electrode power rod 162. The power from the battery is supplied to the electrode unit 140 through the positive electrode power rod 161 and the negative electrode power rod 162. In this regard, when the electrode unit 140 is installed in the first chamber 131, if the control circuit fixing plate 151 and the low plate 154 is fixed by the fixing bolt 156, the positive electrode power rod 161 and the negative electrode power rod 162 are connected to the electrode unit 140 and thus, the electrode unit 140 can be supplied the electric current from a battery.

On the other hand, as illustrated in FIG. 15(*a*), the spraying unit 120 can has a form to control the spraying direction and another form to spray forward as shown in FIG. 15(*b*). Also, in the case of not using the spray, a cap in FIG. 15(*c*) can prevent the sterilized water or the water in the container 111 from leaking outside.

Structured as above, the apparatus for manufacturing sterilized water 100 is assembled as follows.

The body case 130 is assembled with the container 111 made of plastic while the ring 112 is interposed therebetween. Then, the electrode unit 140 is inserted into the first chamber 131 through the open side of the low side of the body case 130. And, in the condition that the control circuit fixing plate 151 is put in the second chamber 132, the control circuit fixing plate 151 overlapped with the low plate 154 is fixed with the circuit fixing plate 151 are fixed to the body case 130 by the fixing bolt 156. Here, the electrode rods 161, 162 are connected to the electrode unit 140 and can supply the electric current from the battery 160 to the electrode unit 140.

When the platinum of the electrode plates 141, 142 of the electrode unit 140 is used up, the electrode unit 140 should be replaced. In this case, a user dissembles the apparatus for manufacturing sterilized water in the reverse of assembling and separates and replaces the support 143 having the electrode unit 140 from the partition 148.

Hereinafter, the principle of the apparatus for manufacturing sterilized water in accordance with the present of the invention will be described.

Manufacturers calculate the best time for sterilizing the water in the container 111 in advance and make the control circuit 152 memorize it before delivering the apparatus for manufacturing sterilized water 100 in the market. After purchasing this apparatus 100 for sterilizing a wound area or a nose with sterilized water manufactured on the spot, a user pours relatively clean water such as tap water or underground water into the container 111. Then, by opening a salt capsule (not shown) with relatively high salinity to make NS of 0.9% salinity with the water and by mixing the capsule with the water in the container 111, the water in the container 111 turns to be the same concentration of NS, i.e., about 0.9% salinity. On the other hands, a normal saline purchased in the market can be used.

Then, the User presses the operation switch 133 for sterilizing the water in the container 111, then, negative electric power and positive electric power are respectively supplied to the negative electrode plates and the positive electrode plates inside of the body case 130 only for a preset time. At this time, 'now operating' message is shown in the indicator 134 to notice that electric power is supplied to the electrode unit. In the case of the container 111 does not include the water, the positive electrode and the negative electrode posed apart from each other automatically stop the electric current flowing, because there is not any medium to flow electricity between the positive electrode 142 and the negative electrode plate 141.

For the preset time, as electric power is supplied, active electrolysis creates oxidants within a short time, and the circulation fan (not shown) in the body case 130 circulates the water to flow out into the container 111 from the first chamber 131. At the same time, in order to emit the heat generated from the electrode unit 140, the ventilated fan (not shown) near to the fins (not shown) rotates and emits the hot air outside through a ventilating opening (not shown) of the body case.

After finishing the water sterilization by oxidants generated from the electrode for a preset time, 'Finished' message is shown in the indicator 134. After finishing the sterilization process, the user can spray the sterilized water to where the user wants. Otherwise, the user can keep the sterilized water by detaching the spraying unit 120, 120' and cover it with a cap and prevent the outside air from intruding in the inside of the case. Therefore, the sterilized water can keep sterilized and clean condition for a relatively long time.

On the other hand, when user wants to manufacture sterilized water again using the apparatus 100 after using it 1 to 10 times, the electric current supplied from the electric supply 160 is reversed. Therefore, the negative electrode and the positive electrode of the electrode unit 140 can keep clean condition without residues attached by electrolysis Also, different recognizing the signal of pushing the operation switch 133 according to one time or two times makes differently control the time sending electric power to the electrode unit 140. That is, as the general water need the more reaction time than the saline water, user can control the time by pushing the operation switch 133 two times or one time according to the type of water. Selectively, the structure which electric power is supplied to only some parts (not all parts) of electrode unit 30 can realize the similar effect to the foregoing.

In other words, as shown in FIG. 12, the apparatus for spraying the sterilized water 100 in accordance with one embodiment of the present invention uses a principle which installs the positive electrode 141 and the negative electrode 142 apart therefrom about a distance within the water 111 of the container 110, and, inducts electrolysis in the water by receiving the electric power through the electric power line 161 from an electric power supply 160 and sterilizes bacteria and viruses using oxidants like ozone, OH radicals generated by the electrolysis. More particularly, the electrode unit 140 in accordance with one embodiment of the present invention can be structured as one of electrodes 140, 240, 340 shown in FIGS. 3 to 9.

Herein, as illustrated in FIG. 12, the apparatus 100 having an electrode unit 140 comprises a container 110 for receiving the water 111, the electrode unit 140 fixed to the ground of the container 110 and an electric power supply 160 supplying the electric power to the electrode unit 140.

The electric power supply 160 can use DC power converted from AC or DC power supplied from a battery. A negative electrode line 161 from the electric power supply is connected to negative electrode plates 141 and a positive electrode line 162 is connected to positive electrode plates 142.

As illustrated in FIGS. 3 to 6, the electrode unit 140 includes negative electrode plates 141 having a plurality of negative electrode projections 141*a* on its surface, positive plates 142 having plurality of positive electrode projections 142*a* and a support 143 fixed to the ground of the container 110 fixing the negative electrode plates 141 and the positive electrode plates 142 passing through the fixing hole 143*a* of the support 143.

Herein, the negative electrode plates 141 and the positive electrode plates 142 are fixed to the support 142 at a distance d1 and have negative electrode projections 141*a* and positive electrode projections 142*a* protuberantly formed like a cone on sides B which face each other at a distance d1 whereby electric charges sent to the electrode plates 141, 142 converge on a fore-end B of projections 141*a*, 142*a*. Therefore, with the same amount of electric power, the negative electrode projections and the positive electrode projection make electrolysis of the water between them more vigorous.

Also, the negative electrode projections 141a and the positive electrode projections 142a are plated with more platinum than other parts so that the electrolysis can be more activated.

As illustrated in FIG. 4, the support 143 includes concave connection slots 1431 for fixing the negative electrode plates 141 and concave connection slots 1432 for fixing the positive electrode plates 142. As shown in FIG. 7, a negative electrode line 161 is connected to the connection slot 1431 of the negative electrode plates 141, and the positive electrode line 162 is connected to the connection slot of the positive electrode plates 142 inside of the support 143 so that simply inserting the electrode plates 141, 142 into the slots 1431, 1432 of the support 143 can provide an environment of supplying electric power to the electrode plates 131, 132. Here, for the convenience, the power supply lines 161, 162 are marked in the side in FIG. 4, but, in actuality, the power is supplied by inserting the electric supply rods 161, 162 in FIG. 12.

When the platinum of the electrode plates 141, 142 is used up, the electrode plates 141, 142 can be separated and new electrode plates 141, 142 are replaced and inserted into the slots 1431, 1432 respectively. Therefore, comprised as above, the apparatus for spraying the sterilized water 100 can be permanently used.

Hereinafter, the apparatus 100 having the electrode unit will be described.

When user wishes to manufacture the water to disinfect and sterilize viruses using the apparatus 100, user pours tap water 111 into a container 100 and sends electric power from the electric power supply 160, then the electric power is supplied to a connection slots 1431 of negative electrode plates 141 and slots 1432 of a positive electrode plates. Then, negative electric power is supplied to the negative electrode plates 141 and positive electric power is supplied to the positive electrode plates 142 through each connection slot 1431, 1432. Here, electric power is sent to the negative electrode plates 141 and the positive electrode plates 12 respectively, and the electric charges converge on the negative electrode projections 141a and the positive electrode projections 142a facing each other in each electrode plate 141, 142. Therefore, the electrolysis between projections 141a, 142a generates oxidants like ozone, H2O2, HOCL, OH radicals actively so that it cleans, disinfects and sterilizes residues, impurities, viruses and bacteria in a short time.

The apparatus 100 needs only the electrode plates 141, 142 having projections 141a, 142a inside of the container so that it can be designed portable size. Here, a controller having a timer to induct electrolysis for a preset time can be included.

On the other hand, as shown in FIG. 7 as another shape of the sectional view of FIG. 12, electrode plates 241, 242 can include branch plates 2411, 2421 from electrode plates 241, 242, and the negative electrode projections 2411a and the positive electrode projections 2421a can be formed in the branch plates 2411, 2421 facing each other at a nearer distance than the electrode plates 241, 242.

The structure as above has advantages of manufacturing sterilized water for a short time and directly using it based on the principle that the more area for electrolysis can be realized.

FIG. 9 is a sectional view illustrating another structure of the electrode in FIG. 12. Compared with the electrode unit 140 in FIG. 3, the electrode unit 140 in FIG. 9 has a feature that comprises a negative electrode 430 supplied negative electric power through a negative electric power line 421 from an power supply 420 and a positive electrode unit 440 supplied positive electric power through a positive electric power line from the power supply 420.

The negative electrode 430 includes two support rods 431 of a negative electrode posed at a distance and connected to a negative power line 421, a negative electrode rod 432 which forms a plurality of rods between the support rod 431 of negative electrode, the negative electrode projections 433 projected like a pillar on the low side of the negative electrode rod 432 to gather electric charges and a fitting projections 434 formed in the low side of the negative electrode support rod 431 to ensure a predetermined distance from the positive electrode 440.

The positive electrode unit 440 comprises two support rods 441 of positive electrode posed at a distance and connected to a positive power line 422, a positive electrode rod 442 which forms a plurality of rods between the support rod 441 of positive electrode, a positive electrode projection 443 projected like a pillar on the upper side of the positive electrode rod 442 to gather electric charges and a fitting groove 444 formed in the upper side of the positive electrode support rod 441 to ensure a predetermined distance from the negative electrode 430.

Structured as above, the electrodes 430, 440 of another type of the apparatus for spraying sterilized water in accordance with one embodiment has the electrode projections 433, 443 formed in the electrode rods 432, 442 so that it can be made by molding, and the loss of electric charges and the cost for the electrodes can be reduced.

Also, as illustrated in FIG. 10, the electrolysis become more active in saline water sot that the apparatus can be structured to manufacture and spray the sterilized water having 0.9% salinity. Moreover, the electrode plates 141, 142 have the projections 141a, 142a so that the sterilizing time will be further shorten by a more vigorous electrolysis. Therefore, the water used for the present invention can include saline water more efficiently as well as tap water, distilled water.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims. That is, exemplary embodiment of the present invention includes electrode projections shaped like a pillar in order to converge electric charges, but the shape is not limited to the pillar shape but should include any shape which can inducts the concentration of electric charges.

INDUSTRIAL APPLICATION

The apparatus for spraying the sterilized water according to the present invention is not limited to a small sized one such as spraying the sterilized water into the inside of a nose, but is extended to a big sized one by manufacturing a large amount of sterilizing water and then spraying it. For example, the container of the apparatus of the present invention can be located at any place in the hospital, and the sterilized water manufactured in the container is to be transferred to lots of medical consultation rooms or treatment tables, and then, the sterilized water can be sprayed or supplied to many patients for their needs by a spraying unit.

Also, it is very obvious for a person ordinarily skilled in the art that the scope of the present invention is not limited to the electrodes' construction shown in the figures, but includes any type of electrode which can induct electrolysis.

The invention claimed is:

1. An apparatus for manufacturing sterilized water comprising:
    a container having a water receiver for accommodating water;
    at least one electrode unit having a negative electrode within the container and a positive electrode within the container, the positive electrode separated from and facing the negative electrode; and,
    a power supply for supplying direct current to the electrode unit immersed under the water, wherein the negative electrode has a plurality of negative electrode projections thereon, and the positive electrode has a plurality of positive electrode projections thereon, each positive electrode projection arranged to face and be aligned with each negative electrode projection one by one to form a current path.

2. The apparatus as claimed in claim 1, wherein the negative electrode and the positive electrode are formed as plate shape respectively.

3. The apparatus as claimed in claim 1, wherein the water is salt solution.

4. The apparatus as claimed in claim 1, wherein the negative electrode projections and the positive electrode projections are formed as one of cones having an acute end or pillars.

5. The apparatus as claimed in claim 1, wherein the negative electrode projections and the positive electrode projections are formed or plated by one of platinum, titanium and carbons.

6. The apparatus as claimed in claim 1, wherein one of the negative electrode projection and the positive electrode projection is formed as replaceable.

7. The apparatus as claimed in claim 1, wherein the power supply is formed as at least one battery, and wherein the apparatus is portable.

8. The apparatus as claimed in claim 1, further comprising a salt receiver for accommodating at least one salt package of which amount is packaged to make the water in the container have a concentration of normal saline.

9. An apparatus for manufacturing sterilized water comprising:
    a pipe;
    at least one negative electrode having a plurality of negative electrode projections within the pipe;
    at least one positive electrode within the pipe having a plurality of positive electrode projections arranged to face and be aligned with each of the negative electrode projections one by one; and
    a power supply for supplying the direct current to the negative electrode and the positive electrode, wherein the negative electrode has a plurality of negative electrode projections thereon, and the positive electrode has a plurality of positive electrode projections thereon, each positive electrode projection arranged to face and be aligned with a negative electrode projection one by one to form a current path.

10. The apparatus as claimed in claim 9, wherein the water is one of tap water, underground water and distilled water.

11. A portable apparatus for manufacturing sterilized salt solution comprising:
    a container accommodating salt solution made by mixing salt with water of one among tap water, underground water and distilled water;
    at least one electrode unit having a negative electrode within the container and a positive electrode within the container separated from the negative electrode and facing the negative electrode; and
    a battery for supplying direct current to the electrode unit, wherein the negative electrode has a plurality of negative electrode projections thereon, and the positive electrode has a plurality of positive electrode projections thereon, each positive electrode projection arranged to face and be aligned with each negative electrode projection one by one to form a current path.

12. The portable apparatus as claimed in claim 11, further comprising a supplier for supplying the sterilized salt solution to human body wherein the supplier includes a tube of which end is immersed under the salt solution so that the sterilized salt solution can be supplied to the human body through the tube.

13. The portable apparatus as claimed in claim 11, further comprising a button for applying the direct current to the electrode unit during the predetermined time.

14. The portable apparatus as claimed in claim 11, wherein the salt solution is normal saline.

15. The portable apparatus as claimed in claim 14, wherein the normal saline is made by putting salt taken out by opening a salt package of which amount is packaged to make the water in the container have a concentration of normal saline.

16. The portable apparatus as claimed in claim 11, wherein the negative electrode projections and the positive electrode projections are formed or plated by one of platinum, titanium and carbons.

17. The portable apparatus as claimed in claim 11, wherein the plated thickness on the negative electrode projections and on the positive electrode projections are formed more thickly than other area.

* * * * *